United States Patent [19]

Enjoji et al.

[11] Patent Number: 4,611,372
[45] Date of Patent: Sep. 16, 1986

[54] METHOD FOR MANUFACTURING AN ULTRASONIC TRANSDUCER

[75] Inventors: Susumu Enjoji; Kazufumi Ishiyama, both of Ootawara, Japan

[73] Assignee: Tokyo Shibaura Denki Kabushiki Kaisha, Japan

[21] Appl. No.: 662,626

[22] Filed: Oct. 19, 1984

Related U.S. Application Data

[62] Division of Ser. No. 565,174, Dec. 23, 1983, abandoned.

[30] Foreign Application Priority Data

Dec. 27, 1982 [JP] Japan .............................. 57-226974
Dec. 28, 1982 [JP] Japan .............................. 57-227265

[51] Int. Cl.⁴ .............................................. H01L 41/22
[52] U.S. Cl. .................................. 29/25.35; 310/327; 310/369
[58] Field of Search ............... 29/25.35; 310/334–337, 310/367, 369, 327, 366

[56] References Cited

U.S. PATENT DOCUMENTS

| | | | |
|---|---|---|---|
| 3,378,705 | 4/1968 | Bacon | 310/9.5 |
| 3,401,276 | 9/1968 | Curran et al. | 29/25.35 |
| 3,950,660 | 4/1976 | McElroy | 310/8.2 |
| 4,101,795 | 7/1978 | Fukumoto et al. | 310/336 |
| 4,156,158 | 5/1979 | Wilson et al. | 310/369 |
| 4,217,684 | 8/1980 | Brisken et al. | 29/25.35 |
| 4,224,547 | 9/1980 | Miller | 29/25.35 X |
| 4,305,014 | 12/1981 | Borburgh | 310/334 |
| 4,370,785 | 2/1983 | Assenza et al. | 29/25.35 |
| 4,395,652 | 7/1983 | Nakanishi et al. | 310/334 |
| 4,446,396 | 5/1984 | Claus | 310/334 |

FOREIGN PATENT DOCUMENTS

843827 8/1960 United Kingdom ............... 29/25.35

*Primary Examiner*—Carl E. Hall
*Attorney, Agent, or Firm*—Finnegan, Henderson, Farabow, Garrett & Dunner

[57] ABSTRACT

An ultrasonic transducer comprising piezoelectric resonators, a matching layer formed on the ultrasonic oscillation surfaces of the resonators, and a backing material adhered on the opposite surface to the ultrasonic oscillation surface, wherein a cylindrical case is fixed to the circumference of the resonators and the backing material is formed by being cast into the case. A method for manufacturing the ultrasonic transducer, wherein the piezoelectric ceramic is temporarily fixed on a metal support and divided into a predetermined shape and a backing material is formed as such that lead wires are allowed to extend through the backing material.

8 Claims, 8 Drawing Figures

METHOD FOR MANUFACTURING AN ULTRASONIC TRANSDUCER

This is a division of application Ser. No. 06/565,174, filed Dec. 23, 1983, now abandoned.

BACKGROUND OF THE INVENTION (a) Field of the Invention

The present invention relates to a method for manufacturing an ultrasonic transducer for an ultrasonic probe device used as medical equipment.

(b) Description of the Prior Art

A piezoelectric ceramic is conventionally used for a piezoelectric resonator as an ultrasonic transducer in an ultrasonic probe. Such a piezoelectric ceramic is divided into ring-, dice- or array-shaped elements in accordance with an intended application of the resultant transducer. In order to obtain array-shaped elements from a piezoelectric ceramic, electrodes are connected to two ends of a piezoelectric ceramic by FPC (flexible printed circuit) plates or the like. Thereafter, a backing material (e.g., a rubber) as a noise absorbent is adhered to the piezoelectric ceramic through the FPC plate. Then, the piezoelectric ceramic is divided into strips of a predetermined size using the backing material as a support.

However, if ring- or dice-shaped elements are desired, it is impossible to connect electrodes or ground terminals from two ends of the piezoelectric ceramic in view of the divided state of the ceramic. For this reason, when electrodes must be connected to the piezoelectric ceramic, lead wires must be inserted to extend through the backing material. Thereafter, the piezoelectric ceramic and the backing material are adhered together, and the assembly must be cut into a predetermined concentric or lattice format with a laser beam. When such a process for manufacturing a transducer is adopted, manufacturing presents difficulties in respect of a positioning precision of lead wires or the like. Furthermore, the processing with the laser beam adversely affects the cut surface of the backing material (generally a rubber) which has a low thermal conductivity. The heat resistance of the adhesive for the backing material must also be considered.

When a ground terminal is to be connected, a method as shown in FIG. 1 has been proposed if a divided piezoelectric ceramic is disc-shaped. According to this method, referring to FIG. 1, a disc-shaped ceramic 2 divided into concentric elements 2a, 2b, 2c and 2d is fixed on a backing material 1. A thin copper foil 3 is soldered across the elements 2a, 2b, 2c and 2d. Ground lead wires are connected to the copper foil 3. In FIG. 1, reference numeral 4 denotes lead wires.

When ground lead wires are connected according to this method, the copper foil on the upper surface of the piezoelectric ceramic causes undesired oscillation to adversely affect the acoustic characteristics of ultrasonic waves generated by the piezoelectric ceramic. When a preformed coating material is adhered on the upper surface of the piezoelectric ceramic to form a matching layer in order to improve acoustic characteristics, the adhesion surface becomes nonuniform due to the soldered copper foil, resulting in defective adhesion. When a coating material of an epoxy resin is coated on the upper surface of the piezoelectric ceramic to form a matching layer, the coating layer will have a uniform thickness upon polishing. However, upon such polishing, the copper foil may be exposed to the surface or become separated, which is not preferable from the viewpoint of safety.

SUMMARY OF THE INVENTION

The present invention has been made in consideration of this and has for its object to provide an ultrasonic transducer divided into ring-, dice- or any other shaped elements wherein electrodes and ground lead wires can be easily connected to a piezoelectric ceramic through a backing material, the backing material whereof does not suffer adverse heat effects upon treatment with a laser beam, and wherein the acoustic characteristics of ultrasonic waves generated by the piezoelectric ceramic are not impaired, and to provide a method for manufacturing such an ultrasonic transducer.

According to an aspect of the present invention, there is provided a method for manufacturing an ultrasonic transducer, comprising the steps of cutting a piezoelectric ceramic into ultrasonic vibrator elements having a predetermined shape with a laser beam or an ultrasonic beam, connecting lead wires to said elements, and covering said elements with a backing material, characterized by further comprising the steps of: temporarily fixing a piezoelectric ceramic on a metal support; dividing the piezoelectric ceramic into ultrasonic resonator elements of a predetermined shape with a laser beam or an ultrasonic beam and connecting lead wires to said elements, respectively; adhering one end of a cylindrical case to a peripheral edge of the piezoelectric ceramic on said metal support; forming a backing material on the piezoelectric ceramic, such that the lead wires extend through the backing material; and removing said metal support.

DETAILED DESCRIPTION OF THE PREFERRED EMBODIMENTS

An ultrasonic transducer and a method for manufacturing the same according to the present invention will now be described with reference to the accompanying drawings.

FIGS. 2 to 5 are views showing steps of a method for manufacturing a disc-shaped transducer.

Figure 1:
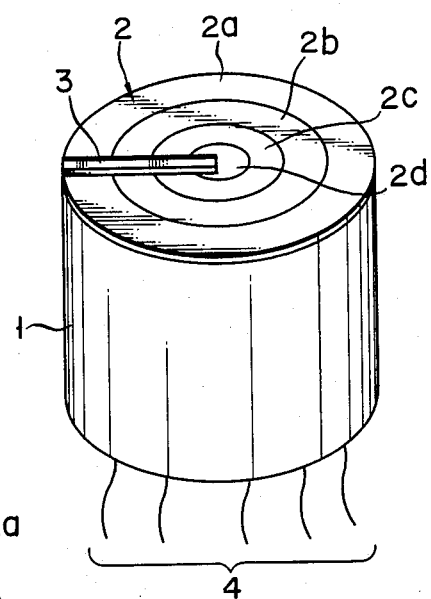
FIG. 1 is a schematic perspective view showing a conventional transducer.
Figure 2:
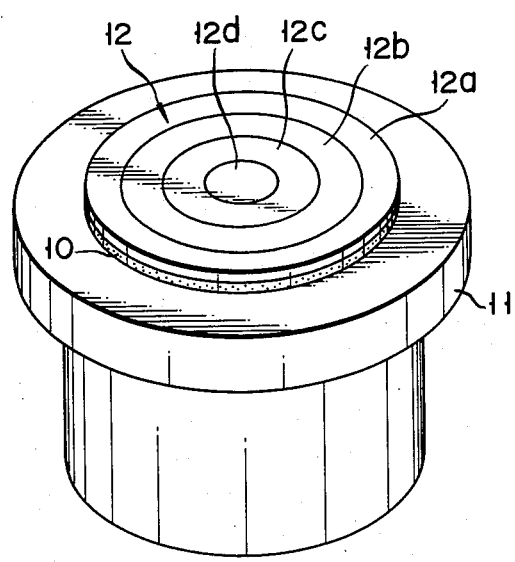
FIG. 2 is a perspective view showing a state wherein a divided piezoelectric ceramic is temporarily adhered on the upper surface of a support.

First, as shown in FIG. 2, a disc-shaped piezoelectric ceramic 12 is temporarily adhered to the upper surface of a metal support 11 by using an adhesive 10 such as wax. Then, the piezoelectric ceramic 12 is divided into concentric ring-shaped elements 12a, 12b, 12c and 12d by a laser beam or an ultrasonic beam. The metal support 11 preferably comprises a material which has a good thermal conductivity such as copper.

Figure 3:
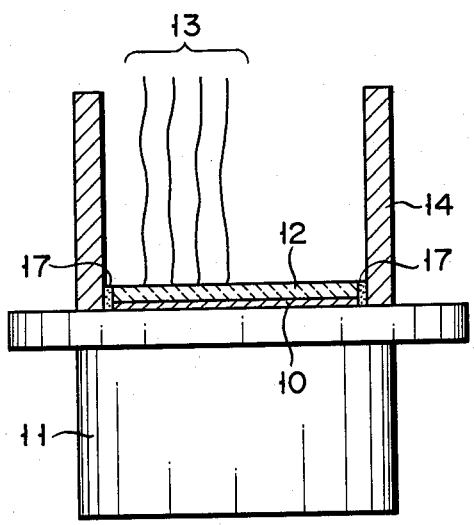
FIG. 3 is a sectional view showing a state wherein the respective elements of the piezoelectric ceramic are wired and a case is bonded thereto.

Subsequently, as shown in FIG. 3, lead wires 13 are soldered and wired to the respective concentric elements 12a, 12b, 12c and 12d adhered to the upper surface of the metal support 11. A cylindrical case 14 made for example of brass is fitted around and adhered to the peripheral edge of the piezoelectric ceramic 12 so that it extends to the upper surface of the metal support 11. The case 14 is adhered with a strong adhesive 17.

Figure 4:
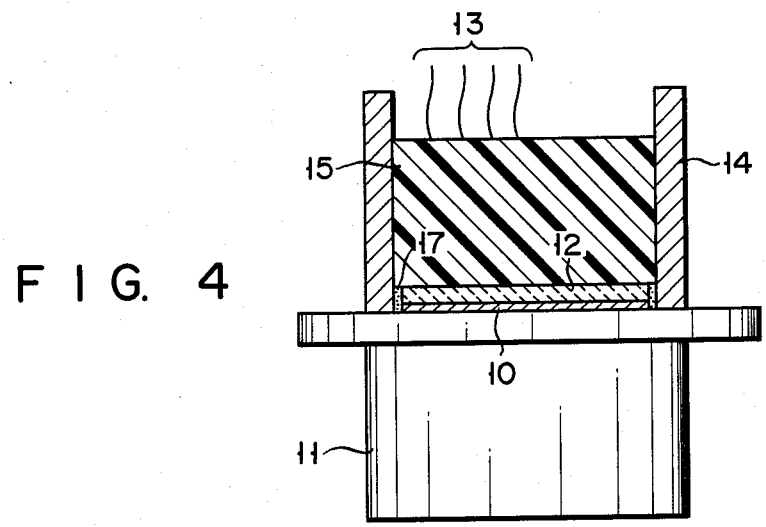
FIG. 4 is a sectional view wherein a backing material is injected into the case.

A backing material 15 in a liquid form is poured or cast into the case 14 fitted around the piezoelectric ceramic 12 and supported on the upper surface of the metal support 11 as shown in FIG. 4. During this process, the lead wires 13 connected to the respective elements 12a, 12b, 12c and 12d of the piezoelectric ceramic 12 are extended upward through the backing material 15 being poured. The backing material 15 is for absorbing ultrasonic oscillation and must be a backing material having a suitable acoustic impedance, attenuation factor and the like. Such a backing material may be, for example, a mixture of an epoxy type adhesive and 60 to 75% by weight of a metal such as a ferrite powder or a manganese-zinc powder.

Figure 6:
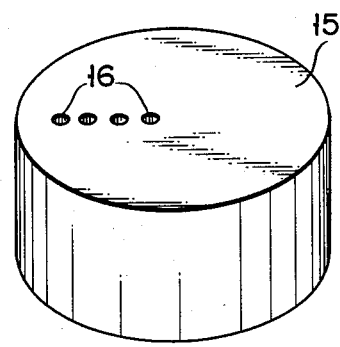
FIG. 6 is a perspective view showing a preformed backing material body.

As the backing material is poured or cast, the piezoelectric ceramic 12 is securely adhered to the backing material 15 and the lead wires 13 can be easily led outside the backing material 15. As shown in FIG. 6, the backing material 15 may alternatively comprise a preformed backing material body. In this case, holes 16 for receiving the lead wires 13 are formed in the preformed backing material body 15. The backing material body 15 with the holes 16 formed therein is fitted inside the case 14 and is adhered to the piezoelectric ceramic 12. Since the holes 16 are formed at the portions of the backing material body 15 which correspond to the wire positions, the lead wires 13 can be easily led outside the backing material 15.

Figure 5:
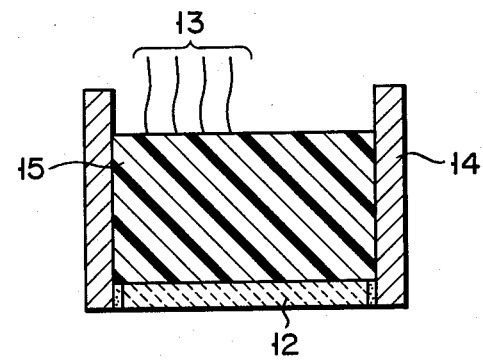
FIG. 5 is a sectional view showing a final product from which the support is removed.

Finally, as shown in FIG. 5, after the piezoelectric ceramic 12 is fixed to the backing material 15, the metal support 11 is removed, thus completing the formation of a disc-shaped transducer.

The lead wires 13 extending through and outside the backing material 15 are connected to a transmission/reception circuit.

The method for connecting ground lead wires to the divided elements of a piezoelectric ceramic according to the present invention will now be described with reference to FIGS. 7 and 8.

Figure 7:
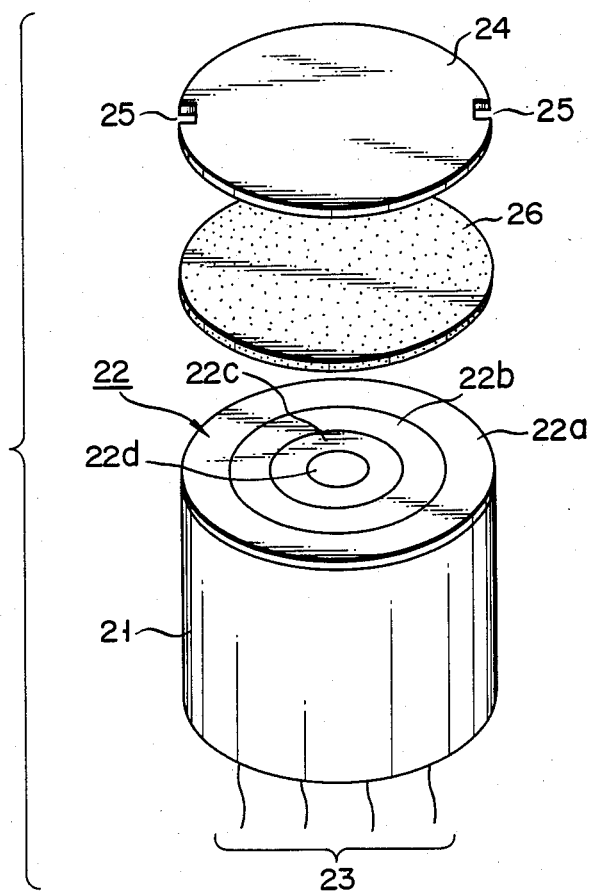
FIG. 7 is a perspective view showing the main part of a disc-shaped transducer according to the present invention.
Figure 8:
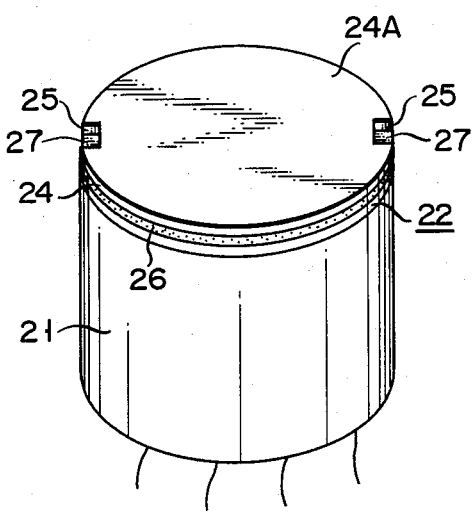
FIG. 8 is a perspective view showing the post-assembly of the transducer shown in FIG. 7.

Referring to FIGS. 7 and 8, reference numeral 22 denotes a piezoelectric ceramic which is divided into concentric ring-shaped elements 22a, 22b, 22c and 22d by a laser beam. The piezoelectric ceramic 22 is fixed to the upper surface of a backing material 21. Lead wires 23 extending through the backing material 21 extend outside the backing material 21 from its lower surface.

Reference numeral 24 denotes a matching layer of an epoxy resin formed on the ultrasonic oscillation surface of the piezoelectric ceramic 22 through a conductive adhesive layer 26. The matching layer 24 is formed to have a predetermined thickness suitable for improving the acoustic characteristics. The predetermined thickness can be ¼ the wavelength λ of ultrasonic waves in the material of the layer 24 as a transmission medium. The matching layer 24 is formed to have a diameter corresponding to the outer diameter of the piezoelectric ceramic 22. Notches 25 are formed at the outer perimeter of the piezoelectric ceramic 22. The conductive adhesive layer 26 may comprise a known conductive adhesive such as "Echo Bond 83C" (Emerson Camming Co., Inc., U.S.A.).

One end of each of ground lead wires 27 is soldered to the corresponding notch 25 of the matching layer 24, as shown in FIG. 8. In this manner, in an ultrasonic transducer of the present invention, a metal layer comprising the conductive adhesive layer 26 is formed on the ultrasonic oscillation surface of the piezoelectric ceramic 22. Accordingly, soldering of the ground lead wires 27 can achieve conduction of the elements 22a, 22b, 22c and 22d. Thus, the ceramic electrodes of the elements can be simultaneously kept at ground potential.

The method of forming the matching layer 24 is not limited to that of the embodiment as described above. Alternatively, after the conductive adhesive layer 26 is applied to the ultrasonic oscillation surface of the piezoelectric ceramic, an epoxy resin can be applied and polished to form a matching layer 24 of the predetermined thickness.

Although the present invention is described with reference to a transducer having ring-shaped elements, it may be similarly applied to a transducer having dice-shaped or array-shaped elements.

According to the present invention, irrespective of the format for dividing a piezoelectric ceramic into ring-, dice- or other shaped elements, electrodes can be connected through lead wires extending through a backing material. Furthermore, since the piezoelectric ceramic is divided by being cut with a laser beam before the backing material is adhered thereto, the backing material is not adversely affected by the heat of the laser beam.

The present invention provides an ultrasonic transducer wherein ground terminals can be easily connected to ring-, dice- or other shaped elements and acoustic characteristics of ultrasonic waves oscillated from the piezoelectric ceramic are not impaired. Since a conductive adhesive has a high acoustic impedance as compared to general adhesives, the thickness of the adhesive layer need not be very precise. The manufacturing method of an ultrasonic transducer can therefore be simplified.

What is claimed is:

1. A method for manufacturing an ultrasonic transducer, comprising the steps of:
   temporarily fixing one surface of a piezoelectric ceramic plate on a surface of a metal support;
   dividing said piezoelectric ceramic plate into a plurality of annular elements by means of a cutting beam irradiated onto a surface of said piezoelectric ceramic plate opposite said one surface;
   connecting a lead wire to each of said annular elements on said opposite surface of said piezoelectric ceramic plate;
   fixing one end of a cylindrical case to a peripheral edge of said piezoelectric ceramic plate fixed on said metal support;
   forming a body of a backing material on said opposite surface of said piezoelectric ceramic plate by casting said backing material in said cylindrical case, said lead wires extending through said cast backing material; and
   removing said metal support from said annular elements.

2. A method according to claim 1, further comprising the step of adhering a matching layer on said one surface of said piezoelectric ceramic plate with a conductive adhesive layer, said conductive adhesive layer providing a common electrical connection to all of said annular elements.

3. A method according to claim 1, wherein said cutting beam is a laser beam.

4. A method according to claim 1, wherein said cutting beam is an ultrasonic beam.

5. A method according to claim 2, further comprising the step of connecting a ground lead wire to said conductive adhesive layer.

6. A method for manufacturing an ultrasonic transducer, comprising the steps of:
   temporarily fixing one surface of a piezoelectric ceramic plate on a surface of a metal support;
   dividing said piezoelectric ceramic plate into a plurality of annular elements by means of a cutting beam irradiated onto a surface of said piezoelectric ceramic plate opposite said one surface;
   connecting a lead wire to each of said annular elements on said opposite surface of said piezoelectric ceramic plate;
   placing and fixing a body of backing material onto said opposite surface of said piezoelectric ceramic plate, said body having a plurality of through holes receiving said lead wires; and
   removing said metal support from said annular elements.

7. A method according to claim 5, further comprising the step of adhering a matching layer on said one surface of said piezoelectric ceramic plate with a conductive adhesive layer, said conductive adhesive layer providing a common electrical connection to all of said annular elements.

8. A method according to claim 7, further comprising the step of connecting a ground lead wire to said conductive adhesive layer.

* * * * *